(12) United States Patent
Harkness et al.

(10) Patent No.: US 10,603,462 B2
(45) Date of Patent: Mar. 31, 2020

(54) TROLLEY FOR THE AUTOMATION OF SLEEP DISRUPTION

(71) Applicant: WASHINGTON STATE UNIVERSITY, Pullman, WA (US)

(72) Inventors: John Hoehn Harkness, Beaverton, OR (US); Ryan Patrick Todd, Vancouver, WA (US); Barbara A. Sorg, Vancouver, WA (US)

(73) Assignee: Washington State University, Pullman, WA (US)

( * ) Notice: Subject to any disclaimer, the term of this patent is extended or adjusted under 35 U.S.C. 154(b) by 213 days.

(21) Appl. No.: 15/689,507

(22) Filed: Aug. 29, 2017

(65) Prior Publication Data

US 2018/0056026 A1    Mar. 1, 2018

Related U.S. Application Data

(60) Provisional application No. 62/380,892, filed on Aug. 29, 2016.

(51) Int. Cl.
*A61M 21/00* (2006.01)
*A61B 5/00* (2006.01)
(Continued)

(52) U.S. Cl.
CPC ..... *A61M 21/0094* (2013.01); *A61B 5/04012* (2013.01); *A61B 5/05* (2013.01); *A61B 5/4806* (2013.01); *A61M 21/00* (2013.01); *A61B 5/4848* (2013.01); *A61B 2503/42* (2013.01); *A61M 2021/0022* (2013.01);
(Continued)

(58) Field of Classification Search
CPC ........ A61M 21/0094; A61M 21/00–02; A61M 2250/00; A61B 2503/40–42
See application file for complete search history.

(56) References Cited

U.S. PATENT DOCUMENTS

2009/0203958 A1* 8/2009 Johnson ............ A61M 21/0094
600/26
2017/0086673 A1* 3/2017 Donohue ............. A61B 5/0051

OTHER PUBLICATIONS

Ramesh et al., "Sleep fragmentation differentially modifies EEG delta power during slow wave sleep in socially isolated and paired mice," Sleep Science, vol. 2 No. 2, Apr. 2009, p. 64-75. (Year: 2009).*

* cited by examiner

*Primary Examiner* — Thaddeus B Cox
(74) *Attorney, Agent, or Firm* — W&C IP

(57) ABSTRACT

The configurations herein are directed to a sleep trolley system for automation of sleep disruption. Such a unique system often includes a platform support system; a natural habitat chamber configured for an animal subject, wherein the natural habitat chamber is removeably disposed thereon the platform support system; an agitator disposed therein the natural habitat chamber, wherein the agitator is configured with a first magnetic component to provide magnetic coupling; a trolley affixed to the platform support system; wherein the trolley is configured with a second magnetic component, wherein the second magnetic component exerts a magnetic attraction force with the first magnetic component coupled to the agitator as disposed therein the natural habitat chamber; and a control system configured to move the trolley along a dimension of the platform support system so as to guide the agitator along a corresponding length of the natural habitat chamber via the magnetic attraction force.

9 Claims, 2 Drawing Sheets

(51) Int. Cl.
 *A61B 5/05* (2006.01)
 *A61B 5/04* (2006.01)
(52) U.S. Cl.
 CPC ............... *A61M 2021/0083* (2013.01); *A61M 2205/106* (2013.01); *A61M 2205/3561* (2013.01); *A61M 2205/3592* (2013.01); *A61M 2205/505* (2013.01); *A61M 2230/10* (2013.01); *A61M 2230/50* (2013.01); *A61M 2230/63* (2013.01); *A61M 2250/00* (2013.01)

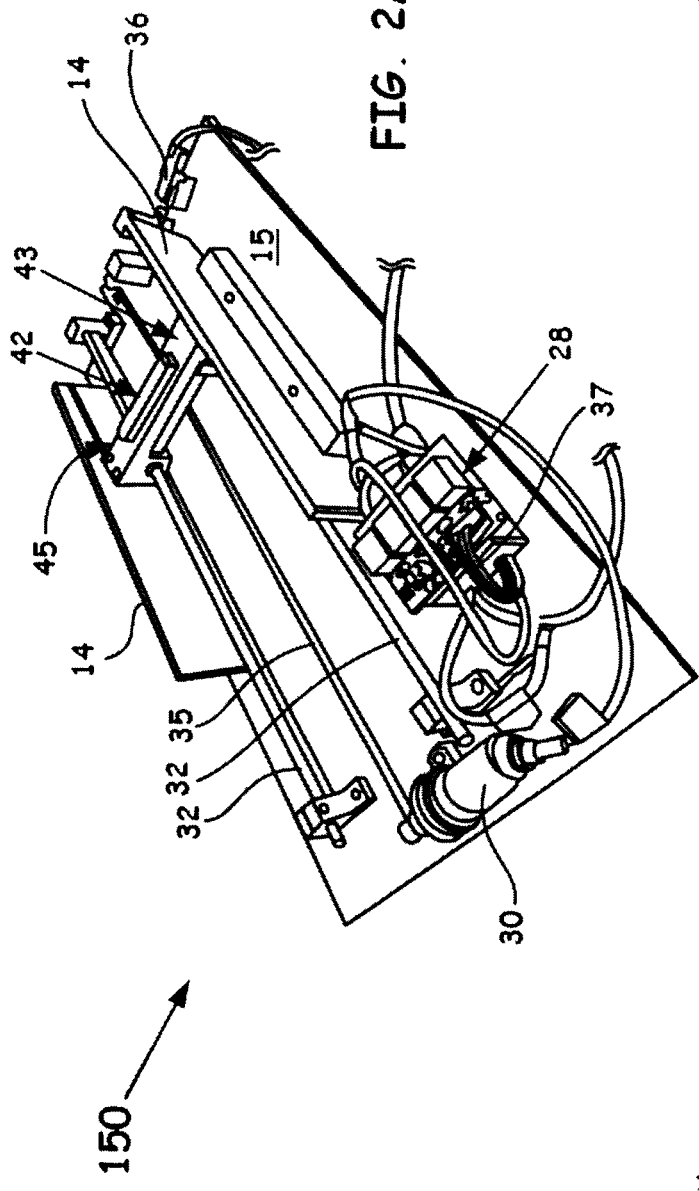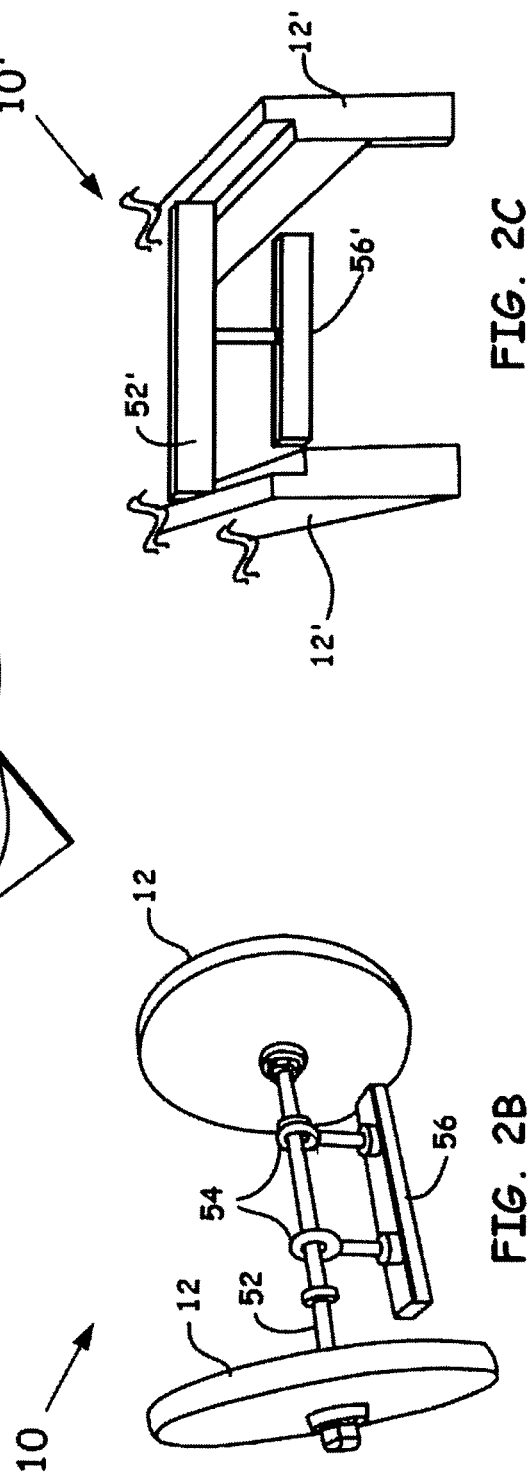

TROLLEY FOR THE AUTOMATION OF SLEEP DISRUPTION

CROSS-REFERENCE TO RELATED APPLICATION(S)

The present application claims under 35 U.S.C. § 119, the priority benefit of U.S. Provisional Application No. 62/380,892, entitled, "Trolley for the Automation of Sleep Disruption," filed Aug. 29, 2016. The disclosure of the foregoing application is incorporated herein by reference in its entirety.

GOVERNMENT INTERESTS

This invention was made with government support under Grant/Contract No. R01DA033404 awarded by the National Institutes of Health. The government has certain rights in the invention.

FIELD OF THE INVENTION

The embodiments herein relate to devices and methods to enable the study of neurological effects resulting from sleep deprivation. In particular, the embodiments herein relate to devices and methods that enable studies in neurophysiology correlated with sleep deprivation in rodents.

BACKGROUND OF THE INVENTION

Discussion of the Related Art

Those of ordinary skill in the art appreciate that at least 7 hours of sleep per night is often sufficient sleep for optimal health in adult humans. However, less than 7 hours of sleep per night amount of sleep is also known to be associated statistically with an increased risk of hypertension, dyslipidemia, cardiovascular disease, metabolic syndrome, type 2 diabetes and depression. Despite such clear counter indications, sleep disruption is an increasingly common concern. A report commissioned by the Centers for Disease Control and Prevention (CDC) tracked changes in sleep habits in the American public from 1985 to 2012. Over this time, the percentage of adults reported to sleep less than 6 hours per night nearly doubled from 38 million to 70 million. Accordingly, additional work on the biological basis for the negative health impacts of sleep deprivation (SD) may offer mitigation strategies.

Sleep deprivation (SD) can be achieved in experimental rodents by applying sensory stimulation. As part of the methodologies, various automated approaches have been applied to minimize the need for experimenter intervention. For example, background material on a system and methodology that uses a rotating bar at the base of the apparatus cage can be found in U.S. Publication Application US2009/0203958A1, entitled, "Apparatus And Method For Automatically Inducing Sleep Deprivation in Rodents," to Johnson et al., filed Feb. 7, 2008, including the following: "Apparatus and method for automatically inducing sleep deprivation in rodents with an electroencephalogram measurement and analysis system, an electromyogram measurement and analysis system, sleep deprivation stimulus, stimulus control, acquisition and real-time sleep stage analysis software, and cage with food and water supplies." As a general principle, the propeller spins about so as to keep the mouse awake but is designed to mimic gentle handling. An existing propeller based design can be provided by Pinnacle Technology Inc.

As another example approach, a research report that utilized a rotating disk over a pool of water to deprive rodents of sleep is described in: Bergmann, B. M. (1995). Sleep deprivation in the rat by the disk-over-water method. *Behavioral Brain Research*, (69), 55-63. Another example approach uses a rotating floor that a rodent stands on, with the floor enclosed within a fixed wall. However, such a sleep deprivation chamber is complex in design and has not been proven in test conditions.

Lafayette Instrument Company also provides a commercial sleep deprivation chamber, wherein the chamber is configured with a sliding bar, which keeps a rodent awake by forcing the animal to step over the moving bar. However, such a design is costly and maintenance of the motor and the track that can result in possible contamination is not desirable. Another existing sleep deprivation system/chamber, as known in the art, includes a treadmill-like configuration wherein a bed with wheel tracks spin for the purpose of sleep deprivation of a disposed rodent. However, this design is also costly and is overtly stressful on the rodent, which can affect results.

It is to thus be appreciated that current rodent sleep deprivation systems and methodologies suffer from systemic introduction of stress to the laboratory animal, electrical interference in EEG recording signals resulting from poorly designed equipment, and inadequate induction of sleep fragmentation. In particular, current systems/methodologies are unable to effectively address environmental novelty, which introduces systemic stress, while also providing a low cost, portable, adaptable to various commercial habitats, low system contamination, sleep deprivation system. With respect specifically to environmental novelty, it is known that rodents are sensitive to environmental novelty (i.e., being placed into a different environmental habitat for studies), and novelty has been shown to induce lasting changes in the brain. As a result, such novelty-induced cellular or molecular changes in the brain confound intended experimental manipulations, thereby masking experimental effects.

Accordingly, there is a need in the art for a methodology and sleep deprivation chamber coupled to a novel platform that does not require the animal (e.g., a rodent) to be removed from its habituated environment and placed into a novel environment. Such a sleep deprivation chamber/platform and methodology also simultaneously addresses cost, contamination, systematic stress (e.g., competitor odor), and adaptability to commercial habitat issues. The embodiments herein are directed to such a need.

SUMMARY OF THE INVENTION

A particular aspect of the embodiments herein is directed to a sleep trolley system for the automation of sleep disruption to include: a platform support system; a natural habitat chamber configured for an animal subject, wherein the natural habitat chamber is removeably disposed thereon the platform support system; an agitator disposed therein the natural habitat chamber, wherein the agitator is configured with a first magnetic component to provide magnetic coupling; a trolley affixed to the platform support system, wherein the trolley is configured with a second magnetic component, wherein the second magnetic component exerts a magnetic attraction force with the first magnetic component coupled to the agitator as disposed therein the natural habitat chamber, and a control system configured to move the trolley along a dimension of the platform support system so as to guide the agitator along a corresponding length of the natural habitat chamber via the magnetic attraction force.

Another aspect of the embodiments herein is directed to a method for the automation of sleep disruption, including: receiving a natural habitat chamber of a subject upon a platform support system; positioning an agitator within the natural habitat chamber of the subject; magnetically coupling the agitator with a trolley affixed to the platform support system, wherein the magnetic coupling is by way of a magnetic attraction force configured with a second magnetic component that exerts a magnetic attraction force with the first magnetic component coupled to the agitator disposed therein the natural habitat chamber; and computer controlling the trolley to move along a dimension of the platform support structure so as to guide the agitator along a corresponding length of the natural habitat chamber via the magnetic attraction force.

Accordingly, the configurations and methodologies herein provide for a unique design that reduces disruption of a rodent. Specifically, the design and methods herein do not require the rodent to be removed from it home cage (natural habitat) and placed into a novel environment, which can confound other experimental variables. Rodents are very sensitive to environmental novelty, and novelty, as known in the art, has been shown to induce lasting changes in the brain. Such changes (cellular or molecular) in the brain could confound the effects of intended experimental manipulations (sleep restriction or sleep deprivation), thereby masking experimental effects.

BRIEF DESCRIPTION OF THE DRAWINGS

FIG. 2A shows an example platform assembly that provides movement for the trolley disposed in the natural habitat chamber of the sleep trolley system for the automation of sleep disruption.

FIG. 2B shows an example wheel-based agitator assembly configured to be disposed within the sleep trolley system for the automation of sleep disruption, as disclosed herein.

FIG. 2C shows an example rail-based agitator assembly configured to be disposed within the sleep trolley system for the automation of sleep disruption, as disclosed herein.

DETAILED DESCRIPTION

Figure 1:
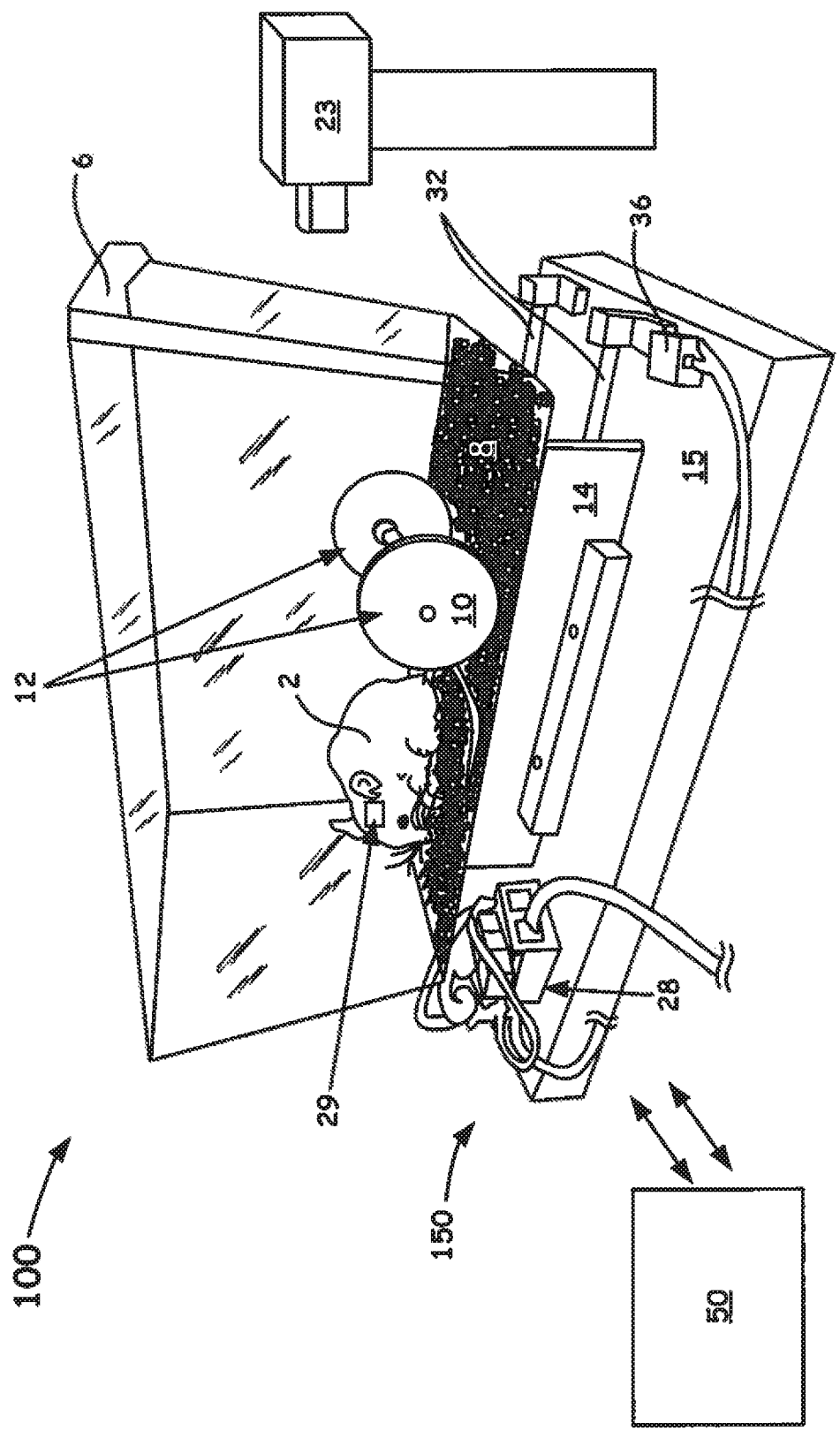
FIG. 1 shows an example sleep trolley system for the automation of sleep disruption, as disclosed herein.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

The embodiments herein provide for a methodology and configuration to disrupt sleep in animals, often to disrupt sleep in rodents (rats). As briefly discussed in the background portion above, current rodent sleep deprivation research suffers from systemic introduction of stress to the laboratory animal, electrical interference in EEG recording signals resulting from poorly designed equipment, and inadequate induction of sleep fragmentation. It is to be noted that sleep disruption (sleep deprivation) via the system and methodologies herein is enabled by use of a novel platform designed to receive an unmodified rodent home cage onto such a platform, the combination of which is unique.

The sleep deprivation chamber itself uniquely is the natural habitat cage of the animal. As a general configuration, the chamber is provided with an easily removeable wheel based agitator configuration, wherein a pair of wheels on a shared axle moves continuously via a magnetically coupled arrangement, as to be disclosed herein, so as to in effect, operate as a magnetic trolley. Efficacy of the methodology in combination with the utilization of the unique chamber, as disclosed herein, was validated by measuring the polysomnographic response of the subject(s) when subjected with, for example, up to at least 6 hours of sleep deprivation in comparison to gentle handling, as known and understood by those of ordinary skill in the art.

Specific Description

Turning now to the drawings, FIG. 1 shows a sleep trolley system for the automation of sleep disruption, generally designated by the reference numeral 100, designed to easily dispose and remove a custom or commercial user-supplied natural habitat chamber 6 onto a platform, as designated by the reference numeral 150 in FIG. 1 but as also shown in more detail in FIG. 2A. As to be discussed in detail below along with other aspects, the core components shown in FIG. 1 for sleep deprivation system 100 thus include the natural habitat chamber 6, the platform 150, the controller and data system 50, and the agitator 10.

It is to be noted that the example chamber shown in FIG. 1 generally depicts a rectangular geometry and thus the platform 150 itself is configured to receive such a rectangular geometry via, in this example arrangement, a pair of supports 14 (only one denoted in FIG. 1 but as best shown in FIG. 2A, as discussed below). However, while the rectangular geometry depicted for system 100 of FIG. 1 is beneficial for illustrative purposes, it is also to be understood that other alternative commercial or custom natural habitat geometries can also be incorporated based on the teachings herein.

For example, the chamber 6 can be non-rectangular geometries such as a square geometry, an elliptical or circular (drum shaped) geometry, etc. Thus, the agitator 10 shown in FIG. 1 can be configured to be coupled to and guided (magnetically) by a reconfigured platform 150 and magnetic trolley (e.g., 45 denoted in FIG. 2A) to comport with such geometries (e.g., moved by a circular trolley based system) without departing from the scope and spirit of the embodiments herein. The overall desire is to provide a sleep deprivation overall system that incorporates the natural habitat of the rodent 2.

With respect to the supports 14, such structures enable the natural habitat chamber 6 to be easily placed thereon and at a prescribed distance above the base 15 of the various components of the platform 150. As part of this design, the required distance enables a desired magnetic coupling (a magnetic attraction force) of the agitator 10 with a magnetic device 42 (as shown in FIG. 2A) provided on a movement trolley 43 (see FIG. 2A) coupled to the base 15 of platform 150.

With respect to the chamber 6 material, it is required that the chamber 6 is configured of a transparent material (a plastic (e.g., a polycarbonate)) to see a test subject (rodent 2) inside it. Moreover, the natural habitat chamber 6 also is required to accommodate all the basic physiological needs of a residing experimental test animal (rodent 2), such as bedding, food, and water (generally denoted by the white reference numeral 8 for clarity within chamber 6). While rodents 2 are the preferred test subject, it is to be understood that other animals (e.g., hamsters, cats, etc.) can also be utilized with an accommodating chamber 6 and platform 150 design as well.

It is also to be noted that, system 100 of FIG. 1 can include one or more motion sensors and one or more cameras (all generally denoted by the reference numeral 23). Moreover, illumination sources are often utilized to aid viewing (not denoted), for monitoring and analyzing physical and biological responses via data processed by controller and data system 50, as generally shown in FIG. 1. Such sensors and/or cameras 23, often can be arranged in a myriad of configurations to collect and generate data for specific responses, such as, but not limited to, physical activities and/or particular responses to agitator 10. The platform 150 can send motion detection and statistical feedback to the controller and data base 58 host. Optional features based on customer specifications include temperature sensing, auxiliary inputs and outputs, inter-platform syncing, and soft starts and stops. Example sensors can include, but are not strictly limited to, infrared (IR) or radio frequency (RF) sensors, as known in the art, to monitor the test subjects (rodent 2) movement and when desired, temperature (rodent 2).

It is also to be noted that sensors to monitor and/or cause sleep disruption can include implants (as generally shown by reference numeral 29), as known in the art, so as to remain or be removed as warranted from a test subject, such as rodent 2, as shown in FIG. 1. Such implants thus often provide desired additional information (data) about the behavioral and the physiological state of the subject (rodent 2). The data provided by such sensors, as is all data obtained by system 100 from any and all sensors, is processed by the controller and data system 50 for overall analysis of the effects of induced sleep deprivation.

The platform 150 itself, as shown in FIG. 2A, is arranged in a novel fashion to provide quiet guided movement of the agitator 10 shown in FIG. 1. The platform 150 configuration includes, but not limited to rails 32, tracks (not denoted), limit switches 36, motor driver means 30, means allowing movement (not denoted), often but not necessarily linear movement, under a dimension of the natural habitat chamber 6. The base 15 of platform 150 is designed to be disposed on a floor or tabletop for ease of use.

The agitator 10 shown in FIG. 2B is configured with a pair of wheels 12, as previously discussed, an axle 52 (bar or support) that couples the wheels, a pair of coupling means (e.g., eyelets 54) and a permanent magnet 56 in this example to extend from the axle 52 a prescribed distance for magnetic coupling purposes. The agitator 10 is thus configured to operate as a magnetically coupled trolley, as discussed below, and is disposed within the chamber 6 with a movement means, often but not necessarily, a wheel based 12 movement means that is designed to substantially extend the width of the example natural habitat chamber 6 shown in FIG. 1. Thus, for the example chamber shown in FIG. 1, the agitator 10 is arranged to move in a linear path along the length of the rodent chamber based on the geometry of the custom or commercially supplied natural habitat chamber 6.

It must be noted however, that while the agitator 10 shown in FIG. 2B is a preferred design, it can also include other movement means such as more than two wheel designs and multiple axles wherein at least one magnet is extending from and coupled to a respective axle of the multiple axles. Another example movement means can, for example, include a sliding mechanism or rail-based/track-based (e.g., guide rails) means.

FIG. 2C thus shows such a rail-based agitator, now referenced by the numeral 10'. However, it is to be noted that the rails depicted are only for illustrative purposes and can be configured similar to the rail-based configuration of the referenced components 32 and 45, as shown in FIG. 2B and as discussed above. In this example, however, FIG. 2C in particular shows a pair of rails 12' that often extends a length or dimension of a chamber 6 (see FIG. 1), a bar or support 52' that couples to the rails 12', and a magnet 56' (e.g., a permanent magnet). The magnet itself thus extends from the bar or support 52' below the support, similar to that as seen in FIG. 2B, via mechanically coupling (e.g., a bar or post) configured with a prescribed distance for magnetic coupling purposes with the trolley 45 of FIG. 2A.

The agitators 10, as shown in FIG. 2B, and 10', as shown in FIG. 2C, are thus configured to operate as a magnetically coupled trolley, as discussed below using the configuration shown in FIG. 2B as a prime example, and is disposed within the chamber 6 with a movement means.

In operation but to reiterate, turning to the agitator 10 (i.e., a linearly-cycling agitator "wheel,") shown in FIG. 2B in particular for teaching purposes, comprised of an axle, often a metal axle 52, substantially the width of the chamber 6, wheels 12, and magnet 56, is placed within the chamber 6. The agitator 10 functions to physically disturb the rodent 2, thus prevent sleep. The agitator 10 moves quietly, in alternating directions (e.g., at approximately 2.54 cm/s in a linear path along the length of the rodent home cage).

It is also to be appreciated that the configuration and the positioning of the example agitator 10 (as well as agitator 10' shown in FIG. 2C) within natural habitat chamber 6 (as best shown in FIG. 1), is beneficial in that the agitator 10 is easily removed from the natural habitat sleep deprivation chamber 6 and easily disposed within natural habitat chamber 6. To reiterate for emphasis, the benefit of such a user portable agitator 10, 10' configuration is that it enables the agitator 10, 10' to be placed in a variety of commercial or custom natural habitat chambers 6, thereby allowing behavioral testing on laboratory animals in their own natural environment.

Accordingly, a rodent 2, for example as the test subject, as illustrated in FIG. 1, does not have to be transferred from the animal's familiar environment to an unfamiliar environment for behavioral testing, thus reducing possible confounding variables such as environmental novelty and competitor odor that could influence behavior and thus influence test results. As an additional benefit, such an agitator configuration allows ease of removal for proper cleaning of the natural habitat chamber 6.

Turning back to the platform 150 discussion, such an example embodiment is often constructed from a rigid but light material to aid portability and manufacture. An example material includes aluminum but can also include other rigid yet light materials (e.g., Polyoxymethylene (POM)) that have high stiffness and excellent dimensional stability where warranted. The base 15 itself, as an example for a system 100, can have dimensions ranging up to at least 10 inches, and as another arrangement greater than 10 inches along a plurality of sides.

In the configuration shown in FIG. 2A, which is for illustrative purposes only, the example platform 150 in the figure can include dimensions of about 25.4 cm×53.34 cm, so as to accommodate a known custom or commercial chamber 6. A trolley 43 is configured with at least one affixed structure with magnetic capabilities (e.g., one or more electro but more often one or more fixed permanent magnets 42). In an arrangement with a permanent magnet 42 affixed to trolley 43 to illustrate a working example embodiment, the configuration is designed to exert an effective magnetic attraction force between the trolley 43 configured on the platform 150 and a coupled material (e.g., a correlated permanent magnet 56 coupled to agitator 10, as shown in FIG. 2B). The magnet 42 coupled to trolley 43 thus forms collectively a magnet trolley 45 to magnetically couple to and guide agitator 10 as the trolley 45 itself is moved by the platform 150 assembly used in system 100. In particular, as trolley 45 moves as directed by motor 30/belt 35/rails 32 arrangement in system 100, and by the trolley 45 exerting a coupling magnetic force to agitator 10, the duo (agitator 10/trolley 45) moves in unison back and forth. As a result, the agitator 10 within chamber 100 moves in a smooth substantially quiet manner to disrupt a disposed rodent 2 of sleep.

As part of the movement means for trolley 45 and magnetically coupled agitator 10, a plurality of fixed rails, often two smooth rails 32 (e.g., 48.26 cm long, 11.11 cm apart), enables in this example embodiment, the aforementioned guided linear movement of trolley 45 back and forth under the length of the chamber 6, as shown in FIG. 1. Actual movement of the magnet trolley 45 (e.g., a 14.6 cm wide magnet trolley), is enabled by a motor 29/belt drive 35 (e.g., a 12 VDC motor-driven belt) in mechanical engagement with the trolley. At either length of the rails 32 are electrical limit switches 36 (only one denoted for simplicity) that detect the arrival of the magnet trolley 45. Shielded DC electronics on the platform communicate over an RJ45 "Ethernet-style" cable 37 with a specially designed and/or commercial controller and data processor 50 (e.g., a computer).

As an example reduction to practice construction, an H-Bridge Driver (generally denoted by reference numeral 28) powers a 12V DC motor 30, which slidably moves the magnet trolley 45 across the rails 32 of the platform 150. As an example arrangement, the motor used in the design is bipolar, which means that the current in the winding needs to be reversed to reverse direction, but is more desired than a unipolar motor of the same weight although alternate motors, such as a unipolar motor is equally capable of being incorporated herein.

The magnet trolley 45, as previously discussed, is capable of both linear and randomized movement across the rail system based on customer preference. At the end of each rail 32, a limit switch 36 is positioned to determine the magnet trolley 45 position. When the limit switch 36 is depressed, the magnet trolley 45 moves in the opposite direction. The controller and data system 50 (e.g., a microprocessor unit (MPU)) or remote host can execute a randomized program that moves by changing polarity of the drive motor at any time, combined with the input of the two limit switches. A motion sensor can also be used to assess the movement of the rodent, and adjust the programmed motion of the trolley.

Such a controller and data system in FIG. 1 (as generally illustrated by reference numeral 50 and a pair of double arrows to connote cross-communication) can thus be in the form of a desktop computer, a laptop computer, a network server, a server computer, or can be implemented by any one of or a combination of general or special-purpose processors (digital signal processor (DSP)), microprocessor units (MPU), firmware, software (also custom or commercial graphical user interfaces (GUI)), and/or hardware circuitry to provide instrument control, data analysis, etc., for the example configurations disclosed herein.

Individual software modules, components, and routines may also be utilized by system 100, as shown in FIG. 10 in the form of the disclosed software program, procedure, or process written in a suitable programming language, e.g., C, C#, C++. In addition, the computer programs, procedures, or processes may be compiled into intermediate, object, or machine code and presented for execution as instructions and control functions, so as to be implemented by system 100.

Various implementations of the source, intermediate, and/or object code and associated data may also be stored in one or more computer readable storage media that include read-only memory, random-access memory, magnetic disk storage media, optical storage media, flash memory devices, and/or other suitable media. As used herein, the term "computer readable storage media" excludes propagated signals, per se and refers to media known and understood by those of ordinary skill in the art, which have encoded information provided in a form that can be read (i.e., scanned/sensed) by a machine/computer and interpreted by the machine's/computer's hardware and/or software.

In other beneficial embodiments, system 100 is connected to other devices over other types of networks, including isolated local area networks and/or cellular telephone networks. The connection can also be a wireless connection or a physical coupling. As non-limiting examples of a wireless connection, such an arrangement can include commercial wireless interfaces, such as but not limited to, radio waves (WiFi), infrared (IrDA), or microwave technologies that also allow integration into available portable personal devices, such as, but not limited to, cell phones, pagers, personal identification cards, laptops, etc. The wireless communication can thus provide signals, including alert messages for expiring blades, etc.

With respect to physical wired coupling, the coupling can be by way of a dedicated coupling I/O means, such as a USB port (not shown), allowing host control of speed, On/Off, and pause. In addition to USB capabilities, optical fibers links can provide, for example, operational data (feedback) via the embedded software (e.g., firmware) or instructions received from or to system 100 via controller and data system 50.

In operation, the controller and data system 50 executes code in response to the limit switches (e.g., limit switch 36, as shown in FIG. 2A), which signals to an electronic relay (generally denoted by reference numeral 28) on the platform, thereby reversing the magnet trolley 45. Trolley speed is regulated by a potentiometer (also generally denoted by reference numeral 28) on the apparatus platform 150. Users are able to control up to 6 Sleep platforms from, for example, one controller and data system 50 (e.g., one computer).

As an illustrative example of executable operation, to begin movement of the agitator 10 wheels 12, a user and/or experimenter selects randomized or linear agitator 10 movement of the wheels 12, selects the intended platform, and clicks to begin movement using, for example, a graphical user interface (GUI). Active movement of the agitator 10 is indicated by the change of a software button color from grey to red. Movement is then stopped at the end of the session by again clicking the appropriate software button. Linear bi-directional movement of the agitator 10 wheels 12 was and is often used during 6-hr experiments, and randomized movement of the agitator was and is often used for the duration of the 12-hr sleep deprivation experiments.

Movement was randomized to change direction or stop movement of the agitator wheel, thus reducing the possibility the rodent habituating to the sound or movement of the agitator 10. Once an unpredicted or "randomized" movement had occurred, the agitator 10 is instructed to complete one full lap of the chamber before randomized movement was again possible. Requiring an agitator 10 travel "reset" between random events eliminated the potential for one end of the chamber to become an undisturbed zone.

To aid the reader in understanding the possible various embodiments of the present invention, the following provides results using various embodiments herein, of which is intended to be illustrative only, but not limiting thereof.

EXAMPLES

Operation Procedure

As an illustrative example procedure, the rodent chamber 6 (to which the rats have been previously habituated) is often placed on the platform 150 with the agitator 10 bar 52 introduced inside the chamber 6 for two days with food and water available ad libitum. The rodent chamber and platform were contained inside a sound- and ambient light-attenuating box (35.56×53.34×86.36 cm), on a 12 h light/dark cycle, with lights on at 07:00. The agitator 10 bar was introduced at the beginning of the light cycle, but did not move during the first 24 h. At the beginning of the second light cycle, the apparatus was activated and agitator bar moved continuously for 6 h. Control rats were housed in identical conditions without movement of the agitator bar. At the end of the 6 h period, rats were perfused and brains removed.

Polysomnographic Instrumentation, Recording and Data Analysis

All experiments were performed under an institutional animal care and use committee-approved protocol and in accordance with National Research Council guidelines and regulations controlling experiments in live animals. Male Sprague-Dawley albino rats were purchased from Simonsen Laboratories at 200 grams. Studies on these rats were completed within one month of their arrival. At all times they were individually housed in LD12:12 conditions at a predetermined temperature of with unrestricted access to food and water.

Rats were instrumented for polysomnographic measurement under isoflurane anesthesia (induction 5%, maintenance 1-3% to maintain breathing at 0.5-1 Hz) using standard laboratory procedures. For the electroencephalogram, screw electrodes were placed in the frontal cortex and parietal cortex. A screw electrode located over the cerebellum served as a ground. For neck electromyogram, wires were embedded bilaterally beneath the nuchal musculature.

Experimental Design

Rats were subjected to overnight acclimation to the tethering and the recording environment. EEG and EMG potentials were collected at 400 Hz beginning at light onset the next morning. Animals were undisturbed during a 24-hr baseline recording session, then subjected to the first of two SD sessions beginning at light-onset: either gentle handling or rolling wheel method, administered in a counterbalanced design. SD was followed by a 6-hr recovery session ending at dark onset, during which animals were allowed to sleep spontaneously. The second SD session was initiated 36 hours after the first. Animals were, in this counterbalanced design, subjected to the opposite SD method from what they experienced in the first SD session.

This session was also followed by a 6-hr recovery session ending at dark onset. After all eight rats had undergone SD by both methods, they were subjected to a terminal experiment. This experiment was conducted 5 days after the most recent SD session for half of the subjects and 19 days after the most recent SD session for the other half of the subjects. Polysomnographic data were collected throughout a final 11-hr session. Four rats were subjected to 11-hr SD via the rolling wheel method, beginning at light onset and euthanized by pentobarbital overdose (50 mg/kg under brief, <1-min, 5% isoflurane exposure) at the end of the 11-hr session. Four rats were allowed to sleep spontaneously for 11 hours and euthanized by pentobarbital overdose (50 mg/kg under brief, <1-min, 5% isoflurane exposure).

Data Collection and Processing

EEG and EMG potentials were collected at 400 Hz using the Pinnacle Technology rodent polysomnographic system (Lawrence, Kans., USA). Data were converted to European data format (edf) by Pinnacle Technology Sirenia software. 10-sec epochs of data were classified as either wake, rapid eye movement sleep (REMS) or slow wave sleep (SWS) with Neuroscore 3.0 software. EEG spectral data were processed with the MATLAB computing language. Data were high-pass filtered at 0.01 Hz and band-stop filtered at 60 Hz with the MATLAB filter function. EEG data were subjected to discrete fourier transform using the MATLAB fft function. Slow wave activity during SWS (SWA; EEG power in the 1-4 Hz range) was normalized to the average SWA value across all epochs of SWS in the baseline 24-hr recording immediately prior to the first SD session. For the purpose of calculating mean episode durations and the total number of episodes, an episode of any given state was initiated by at least three consecutive epochs of a given state and terminated by a single epoch of any other state. Instances where only one or two consecutive epochs of a state occurred were thus not included in tallying episode numbers or episode mean durations. Sleep state timing and EEG parameters were populated onto spreadsheets via a custom MATLAB algorithm and were then subjected to statistical analyses.

Immunohistochemistry

Upon reaching complete unresponsiveness from pentobarbital overdose, rats were perfused transcardially with using 150 mL 1×PBS per rat at a rate of 300 mL/min. Perfusate was switched to 4% paraformaldehyde and perfused at the same rate for at least 250 mL/rat. Brains were removed, immersed in 20 mL 4% paraformaldehyde overnight, and then immersed in 20% sucrose in PBS solution and refrigerated. After two days in sucrose solution, brains were frozen at −20° C. and kept frozen until sectioned.

Coronal prefrontal cortex (PFC; +4.0 through +3.6 from bregma) sections were collected on a freezing microtome at 40 µm for a 1:8 section series. Triple-staining was performed by first washing a single series of free-floating sections three times for 5 minutes in PBS. Tissue was then quenched in 50% ethanol for 30 minutes. Sections were then washed in PBS three times for 5 minutes each, before being placed in a blocking solution containing 3% normal goat serum (Vector Laboratories) for 1 hour. Subsequently, tissue was co-incubated with rabbit-anti-PV (1:1000; ThermoFisher Scientific) and mouse-anti-8-oxo-dG primary (1:350; EMD Millipore) antibodies at 4° C. overnight. Tissue was then rinsed in PBS three times for 10 minutes each, and incubated for two hours in secondary antibody (goat anti-rabbit Alexa Fluor® 405 for the PV antibody, and goat anti-mouse Alexa Fluor® 594 for the 8-oxo-dG antibody). Again, tissue was washed in PBS three times for 10 minutes each, and then incubated with *Wisteria floribunda* agglutinin (WFA; 1:500; Vector Laboratories) at 4° C. overnight. After three 10 minute washes in PBS, sections were transferred to mounting media and then mounted onto Superfrost Plus slides, and allowed to dry overnight. After drying, ProLong Gold Antifade Mountant (ThermoFisher Scientific) was applied to the slides before cover slipping. Slides were stored flat and allowed to dry for three days before imaging.

Quantification of Immunohistochemical Images

Imaging was performed on a Leica SP8 laser scanning con focal microscope with an HCX PL apo CS, dry, 20× objective with 0.70 numerical aperture. The 405, 488, and 594 nm lasers were used for excitation, and were detected by three separate photomultiplier tubes in the 400-450, 460-510, and 590-640 nm ranges, respectively. Calibration of the laser intensity, gain, offset, and pinhole settings were determined within the orbitofrontal cortex (OFC) of a control animal, as this region most reliably expresses strong WFA staining. These settings were maintained for all images. Images were collected in z-stacks of 20 images each (step size 0.44 µm; containing the middle 8.45 µm of each 40 µm section), encompassing the prelimbic PFC and OFC.

All images were compiled into summed images using and scaled, and converted into 8-bit, grayscale, tiff files. PIP-SQUEAK was run in "semi-automatic mode" to select ROIs to identify individual PV+ cells, PNNs, and 8-oxo-dG-tagged cells, which were then proof-read by a trained experimenter. Single-, double-, and triple-labeled neurons were then identified.

Discussion of Results

Sleep Loss and Recovery: Comparison of 6-hr GHSD and 6-hr Rolling Wheel

Under baseline conditions, animals spent 224±48 min in slow wave sleep and 34±18 min in REMS across the 6-hr interval beginning at lights-on (ZT0-ZT6). Both experimental conditions (baseline vs. GHSD vs. rolling wheel) had highly significant main effects on time spent in SWS ($F_{2,14}=54.8$, $P<0.00$) and REMS ($F_{2,14}=21.0$, $P<0.001$). Sleep loss was a result of increased time spent in both intermediate wake ($F_{2,14}=58.9$, $P<0.001$) and active wake ($F_{2,14}=14.4$, $P<0.001$; Table 1).

Time spent in quiet wake was not significantly increased in either SD condition relative to baseline ($F_{2,14}=1.5$, $P=0.260$; Table 1). There was a significant condition X time interaction affecting SWS ($F_{10,70}=3.5$, $P<0.001$) but not REMS ($F_{10,70}=0.157$). SWS occurred with increasing frequency across time in SD (FIG. 1), to a greater extent in the RWSD condition than in the GHSD condition. Consequently, the amount of SWS was significantly greater in RWSD than GHSD during hours 2-6 of SD. Although time X condition interaction was not significant for REMS, REMS was detected in 2, 3 and 5 rats, respectively, in the final 3 hours of RWSD (FIG. 1B). No REMS was detected throughout the duration of the 6-hr GHSD session In the 6-hr interval subsequent to SD sessions, the amount of SWA in the EEG during SWS was elevated dramatically relative to the baseline condition. ANOVA yielded a significant main effect of condition ($F_{2,14}=57.7$, $P<0.001$), as SWA was significantly elevated in SWS subsequent to both GHSD (by 45±8% in hr 1 post-SD) and RWSD (by 25±5% in hr 1 post-SD) relative to baseline (FIG. 2B). There was additionally a time X condition interaction. Although EEG SWA during SWS was elevated in both SD conditions relative to baseline in all of the 6 hrs of post-SD recording, it was elevated to a greater extent in GHSD than in RWSD during hours 1-2 post-SD. After this time, SWA was elevated to the same extent in both GHSD and RWSD relative to baseline.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

The invention claimed is:

1. A sleep trolley system for an automation of sleep disruption, comprising:
 a platform support system;
 a natural habitat chamber configured for an animal subject, wherein the natural habitat chamber is removably disposed thereon the platform support system;
 an agitator disposed therein the natural habitat chamber, wherein the agitator is configured with a first magnetic component to provide magnetic coupling;
 a trolley affixed to the platform support system, wherein the trolley is configured with a second magnetic component, wherein the second magnetic component exerts a magnetic attraction force with the first magnetic component coupled to the agitator disposed therein the natural habitat chamber; and
 a control system configured to move the trolley along a dimension of the platform support system so as to guide the agitator along a corresponding length of the natural habitat chamber via the magnetic attraction force.

2. The sleep trolley system of claim 1, wherein the platform support system is configured to receive the natural habitat chamber, wherein the natural habitat chamber has a geometry selected from: a square geometry, a rectangular geometry, an elliptical geometry, or a circular geometry.

3. The sleep trolley system of claim 1, wherein the agitator is configured as a wheeled apparatus, comprising:
 a pair of wheels;
 an axle coupled to the pair of wheels; and wherein the second magnetic component is configured to be coupled to the axle.

4. The sleep trolley system of claim 1, wherein the agitator is configured as a wheeled apparatus, comprising:
   at least two wheels and at least two axles; and
   wherein at least one magnet is extending from and coupled to a respective axle of the at least two axles.

5. The sleep trolley system of claim 1, wherein the agitator further comprises a rail-based system, comprising:
   a support;
   a pair of guide rails coupled to the support; and wherein the second magnetic component is configured to be coupled to the support.

6. The sleep trolley system of claim 1, wherein the platform support system further comprises:
   a pair of rails slidably coupled to the trolley;
   a belt drive coupled to a motor and additionally coupled to the trolley, wherein the belt drive as directed by the motor, mechanically engages the trolley and moves the trolley along the length of the rails in one direction, and wherein a limit switch directs the motor to reverse rotation so as move the trolley via the belt drive along the length of the rails in an opposite direction.

7. The sleep trolley system of claim 1, wherein the control system is configured to selectively control a random and/or a linear travel of the trolley and the magnetically coupled agitator in relation to the platform support system.

8. The sleep trolley system of claim 7, wherein the control system directs the random and/or a linear travel by controlling operation of a belt drive coupled to a motor that is mechanically engaged with the trolley.

9. The sleep trolley system of claim 1, wherein the first magnetic component is a permanent magnet or an electromagnet and wherein the second magnetic component is a permanent magnet or an electromagnet.

* * * * *